(12) United States Patent
van Dongen et al.

(10) Patent No.: US 6,686,165 B2
(45) Date of Patent: *Feb. 3, 2004

(54) RECOGNITION OF TUMOR-SPECIFIC GENE PRODUCTS IN CANCER

(75) Inventors: Jacobus Johannes Maria van Dongen, Nieuwerkerk aan den IJssel (NL); Vincent Henricus Johannes van der Velden, Capelle aan den IJssel (NL); Paulus Benjamin Berendes, Heerlen (NL); Adriana Cornelia van Denderen, Gouda (NL)

(73) Assignee: Erasmus Universiteit Rotterdam, Rotterdam (NL)

(*) Notice: Subject to any disclaimer, the term of this patent is extended or adjusted under 35 U.S.C. 154(b) by 0 days.

This patent is subject to a terminal disclaimer.

(21) Appl. No.: 09/752,635

(22) Filed: Dec. 29, 2000

(65) Prior Publication Data

US 2002/0042056 A1 Apr. 11, 2002

Related U.S. Application Data

(63) Continuation-in-part of application No. 09/443,546, filed on Nov. 19, 1999, which is a continuation of application No. PCT/NL98/00289, filed on May 20, 1998.

(30) Foreign Application Priority Data

May 20, 1997 (EP) .............................................. 97201507

(51) Int. Cl.[7] ........................ G01N 33/53; G01N 33/574
(52) U.S. Cl. ........................ 435/7.1; 435/7.2; 435/7.21; 435/7.23; 530/388.8; 530/389.7
(58) Field of Search ................................ 435/7.2, 7.23, 435/7.21, 7.1, 810; 530/388.8, 389.7

(56) References Cited

U.S. PATENT DOCUMENTS

| | | | |
|---|---|---|---|
| 5,369,008 A | * 11/1994 | Arlinghaus et al. | 435/7.23 |
| 5,968,734 A | * 10/1999 | Aurias et al. | 435/6 |
| 6,083,709 A | * 7/2000 | Reynolds et al. | 435/7.94 |
| 6,150,110 A | * 11/2000 | Fletcher et al. | 435/6 |

FOREIGN PATENT DOCUMENTS

| | | |
|---|---|---|
| WO | WO 89/11101 | * 11/1989 |
| WO | WO 91/07489 | 5/1991 |
| WO | WO 95/31545 | 11/1995 |
| WO | WO 96/18906 | 6/1996 |

OTHER PUBLICATIONS

Nagasaki et al., "An enzyme immunoassay for carcinoembryonic antigen (CEA) with homogeneous reactivity to different CEA preparations and low cross–reactivity with CEA–related normal antigens", *Journal of Immunological Methods*, vol. 162, No. 2, 1993, pp. 235–245.

* cited by examiner

Primary Examiner—Carla J. Myers
(74) Attorney, Agent, or Firm—TraskBritt

(57) ABSTRACT

The invention relates to the field of cancer diagnosis and the application of diagnostic techniques in pathology and hematology. Specifically, the invention relates to flow cytometric techniques for the detection of chromosomal aberrations and the detection of tumor specific gene products exclusively expressed by tumor cells containing said chromosomal aberrations. The invention provides a method to detect chromosomal aberrations in a biological sample via the exclusive detection of tumor-specific gene-product using at least two different probes directed against the gene-product.

25 Claims, 4 Drawing Sheets

RECOGNITION OF TUMOR-SPECIFIC GENE PRODUCTS IN CANCER

CROSS-REFERENCE TO RELATED APPLICATIONS

This application is a continuation-in-part of co-pending U.S. application Ser. No. 09/443,546 filed Nov. 19, 1999 which claims priority to and is a continuation of International Application No. PCT/NL98/00289, filed on May 20, 1998, designating the United States of America, the contents of which are incorporated by this reference, which PCT International Patent Application itself claims priority from European Patent Office Application Ser. No. 97201507.7 filed May 20, 1997.

TECHNICAL FIELD

This invention relates to the field of cancer diagnosis and the application of diagnostic techniques in pathology and hematology. Specifically, the invention relates to techniques that indicate the presence of chromosomal aberrations by detecting tumor-specific gene products that are exclusively expressed by tumor cells containing the chromosomes.

BACKGROUND OF THE INVENTION

Chromosomal abnormalities or aberrations are a leading cause of genetic disorders or diseases, including congenital disorders and acquired diseases, such as malignancies. Malignant cells have a common clonal origin as they are believed to originate from a single autonomously growing cell that withdrew from environmental growth regulating signals.

The term 'cancer' comprises a heterogeneous group of neoplasms, in which each type has its own characteristic when considering its malignant potential and its response to therapy. Currently, the effectiveness of cancer treatment is empirically determined. Depending on the moment in time in the development of cancer, the origin and spread of the cancer, and on the physiological condition of the patient, the most proper and most effective treatment is selected. At present, selections from surgical treatment, radiation therapy and chemotherapy (or combinations of the former therapies) can be made. Yet, it is realized that each therapy bears side-effects that compromise the benefits of treatment enormously. It goes without saying that accurate diagnosis of the various cancer types is pre-eminent in helping select the most effective therapy.

The basis of cancer stems from chromosomal aberrations such as translocations, inversions, insertions, deletions and other mutations within or among chromosomes. Often, one chromosome or two different chromosomes are involved in the development of malignancies. In this way, genes, or fragments of genes are removed from the normal physiological context of the non-aberrant chromosome and fuse with or find a location in a recipient chromosome, (be it the same or a second chromosome) adjacent to non-related genes or fragments of genes (often oncogenes or proto-oncogenes), where the new genetic combination can be the foundation of a malignancy.

Rearrangements, such as translocations happen often in a somewhat established pattern, where genes, or fragments thereof, are removed from the non-aberrant chromosome at a breakpoint or breakpoint cluster region, and are inserted in the recipient chromosome at a fusion region, thereby creating rearranged, deleted, translocated or fused genes that are specific for that specific cancer. Moreover, rearrangements or translocations can be reciprocal, in that two chromosomes exchange parts which leads to cells containing two, reciprocally rearranged chromosomes which both contain new fused genes.

When the fused gene is translated, it generates a gene-product, mRNA, that is unique for the tumor. The chimeric mRNA comprises parts or fragments of two mRNA's that correspond to and were originally transcribed by the originally separated genes. This tumor-specific mRNA is uniquely characterized by a fusion point, where the RNA fragments meet. In some cases, these fusion points can be detected by hybridizing nucleic acid probes. However, considering the large variation within the individual rearrangements seen in these translocations and depending on the localization of the breakpoint within the non-aberrant gene wherein (even when the translocations occur within the same two genes) different tumor-specific genes can be generated, it is deemed likely that within each separate case of these types of cancer, new fusion points arise. Detection of cancer by specific detection of the fusion-point of the tumor-specific gene-product (mRNA) has therefore never been widely applicable.

When the fused gene is fused in frame, the fused mRNA is translated into a fusion protein that is unique for the tumor. The protein comprises parts of two proteins that correspond to and were originally transcribed by and translated from the originally separated genes. Tumor-specific proteins are uniquely characterized by a fusion point, where the two proteins meet. Fusion points are antigenically exposed, comprising distinct epitopes which sometimes can be immunologically detected. However, considering the large variation within the individual rearrangements seen in these translocations and depending on the localization of the breakpoint within the non-aberrant gene wherein (even when the translocations occur within the same two genes) different tumor-specific genes can be generated, it is deemed likely that within each separate case of these types of cancer, new fusion points arise. Detection of cancer by specific detection of the fusion-point epitope of the tumor specific protein has therefore never been widely applicable. The tumor-specific gene products (fusion products) of the fused or rearranged genes may contribute to the further development of the cancer.

An area where chromosomal aberrations are relatively well studied (as compared with other cancer types) is the field of leukemia. Comparable to most malignant tumors, leukemias differ in the degree of differentiation of tumor cells. According to clinical presentation, leukemias are divided in to acute and chronic forms, depending on the rapidity with which they evolve and, if untreated, cause death.

Depending on the cell lineage(s) involved in the leukemic process, acute leukemias are classified as acute lymphoblastic leukemias (ALL) and acute non-lymphoblastic leukemias (ANLL), with ALL the most predominant type (>80%) occurring in childhood. Chronic leukemias are malignancies in which the uncontrolled proliferating leukemic cells are capable of maturation. Two subtypes of chronic leukemia are distinguished, chronic lymphocytic leukemia (CLL) and chronic myeloid leukemia (CML). Within these four groups, a considerable heterogeneity in biology and prognosis is seen, which currently is stratified along morphological features. This stratification bears, as yet, little value as to an understanding and prediction of the prognosis of a leukemic patient and to rational therapy design.

However, recent molecular genetic studies of leukemic patients have shown that a wide variety of chromosomal aberrations can be found with the various forms of leukemia. One group consists of immunoglobulin (IG) or T-cell receptor (TCR) gene rearrangements, comprising antigen-receptor gene rearrangements that go beyond the normal, physiological processes that are required to generate the diversity of the antigen receptor molecules which typify the lymphoid cell population. In one large group of IG and TCR rearrangements known to be associated with leukemia, tumor specific antigen receptor molecules are expressed. Another group of aberrations comprise deletions of a whole gene or parts of a gene from a genome. As a result of the deletion, promotor regions normally belonging to the now deleted gene can exert control over another gene, resulting in aberrant transcription the gene. An example is the deletion of the coding regions of the SIL gene in T-cells, resulting in the transcription of the normally not expressed TAL-1 gene in T-cells, resulting in ectopic expression of TAL-1 fusion protein. Yet another group comprises translocations of gene fragments between chromosomes, resulting in fusion genes that may well transcribe unique fusion proteins that contribute to the development of the malignancy. Well known examples are the translocations resulting in BCR-ABL fusion genes found in >95% of cases of CML and in 30% of cases of adult ALL and TEL-AML1 which is found in 25–30% of cases of childhood ALL. However, many more fusion genes, such as E2A-PBX1, ETO-AML1 and PML-RARa are known.

Chromosomal aberrations can be detected by a wide array of techniques, various of which entail modern biomolecular technology. Traditional techniques such as cytogenetic analysis by conventional chromosomal banding techniques are, although highly precise, very labor intensive, require skilled personnel, and are thus expensive. Automated karyotyping is useful for some diagnostic applications, such as prenatal diagnosis, but is ineffective in analyzing complex characteristics of malignancies. Furthermore, it is possible to detect increased activity of proteins, for example tyrosine-kinase activity (see, PCT International Publication WO 95/31545) in tumor specific cells. The foregoing techniques require fresh cells, which are not always available.

Other, more modern, techniques using Southern blotting or other nucleic acid hybridization techniques or amplification techniques such as PCR, for detecting well-established chromosomal aberrations for which suitable nucleic acid probes or primers are available. With these techniques, fresh or frozen cells can be used, and sometimes even older samples which have been stored appropriately (such as after formalin fixation), as long as the nucleic acid to be hybridized or amplified remains accessible and intact. However, even with this modern technology, several disadvantages can be found that hamper the application of these diagnostic techniques in the rapid screening for chromosomal aberrations related to such malignancies.

For instance, Southern blotting takes 3 to 4 weeks, which is much too slow to permit therapeutic intervention in malignancies, and allows only 10–15 kb of nucleic acid to be analyzed per probe analysis.

PCR, although in essence well-suited for rapid and massive diagnostic testing or even screening, allows for the analysis of only 0.1 to 2 kb of nucleic acid (DNA or RNA) per PCR analysis, which greatly hampers the rapid screening of vast stretches of chromosomes and breakpoint cluster or fusion regions within the chromosomes or their gene-products. An additional disadvantage of PCR is its inherent sensitivity to mismatched primers. Small, normal and physiological, alterations which can always be present in the nucleic acid sequence of the gene fragment complementary to the primer will make it impossible to operate the PCR with the wanted effect and may result in misdiagnosis and false-negative results. Especially false-negative results render a PCR-based diagnostic test, albeit very specific, insufficiently sensitive for reliable diagnosis, and it goes without saying that only a reliable diagnosis of malignancies can contribute to an understanding of the prognosis and the design of an adequate therapy.

Fluorescent in situ hybridization techniques (FISH) are not so strongly dependent on the exact matching of nucleic acid sequences to get positive diagnostic results, but can only be employed for the detection of chromosomal DNA and not for the detection of the gene-products of the chromosomes. In general, FISH employs probe analysis with large, mainly unspecified, nucleic acid probes that hybridize, however often with varying stringency, with the genes or gene fragments located in the rearranged chromosome in the malignant cell. Using large probes renders the FISH technique very sensitive. The binding of the probes is detected by subsequent detection of the probes with (often multiple) fluorochromes via microscopic observation of a population of cells obtained from the tested sample.

However, even the currently used FISH protocols have inherent disadvantages, mainly relating to the selection of nucleic acid probes employed in the current FISH protocols, often resulting in false-positive results in the diagnosis of chromosomal aberrations, resulting in diagnostic tests that are, although sensitive, not very specific, at least not specific enough to employ standard FISH techniques in massive or rapid diagnostic testing, let alone in automated testing or screening. A false-positive result necessitates cumbersome re-testing of patients, or even unsuspecting clients that have been submitted to routine screening protocols, and can greatly alarm these people.

Immunological detection of the fusion proteins resulting from chromosomal aberrations has, although widely tried, never been successful. This failure is caused mainly by the fact that it is hard to find immunological reagents that are exclusively reactive with tumor-specific proteins contrary to immunological detection of non-fusion proteins that are normally also produced by the body, albeit at a lower level (see, for example, Nagasaki et al., *J. Imm. Methods* 162, 235–245, 1993). Usually, such antibodies cross-react with normal cellular proteins. Only when specific fusion points are known, may it be possible to select specific immunological reagents that react exclusively with the tumor-specific protein, by selective binding to the fusion point epitope. However, the variation in fusion points is so large that specific immunological detection only works in a few occasions, often solely on a patient-by-patient basis.

Furthermore, the identified diagnostic tests have the great inherent disadvantage that they require specialized and well equipped laboratories and trained and highly skilled personnel. Furthermore, these tests are only used in suspected cases of malignancies, and are not suitable for large scale screening of populations at risk for the presence of chromosomal aberrations. Large scale and preventive screening may lead to the early detection of malignancies, after which the often fatal course of a malignancy can be intercepted in an early phase of its development.

DISCLOSURE OF THE INVENTION

The present invention now provides a method to be used in diagnostic testing of biological samples such as blood samples, serum samples, samples of cells, tissue samples, bone marrow, biopsies, for chromosomal aberrations. The invention provides a method to be used in diagnostic testing where both a high sensitivity as well as a high specificity is required. The invention provides a method that can optionally be performed in routine laboratories by personnel with ordinary skills.

The present invention is characterized by a method of detecting chromosomal aberrations in a biological sample via the exclusive detection of tumor-specific gene-product using at least two different probes directed against the tumor-specific gene-product originating from the chromosomal aberration. A surprising advantage of the invention is that it provides a method of detecting chromosomal aberrations related to a wide array of types of cancer, for example, the invention provides a method to detect chromosomal aberrations related to leukemia.

The invention provides a method to detect tumor-specific gene products of various types of chromosomal aberrations. For example, the invention provides a method to detect gene-products corresponding to the fused genes found in chromosomal deletions, inversions or translocations. As an example of the invention a method is provided of detecting the Philadelphia chromosomal aberration found in leukemias. The invention provides a method of detecting tumor specific gene-products such as tumor-specific mRNA as well as tumor-specific protein. The probes used by the invention are optionally adjusted to the nature of the gene product, mRNA detection is provided by using at least two different nucleic acid probes, each being reactive with distinct sites on the gene-product. Tumor-specific protein detection is provided by using as probes at least two different binding-proteins, each being reactive with distinct sites on the gene product. As binding proteins, a wide array of proteins is known in the art, such as receptor molecules, polyclonal or monoclonal (synthetic) antibodies, binding peptides or 'phage' antibodies derived via phage display techniques, and so on. By using antibodies, the invention provides a method to detect chromosomal aberrations immunologically.

As an example of the invention, a method is provided wherein the tumor-specific gene-product is detected by a sepharose-Western blotting procedure. As a yet another example of the invention, a method is provided wherein the tumor-specific gene-product is detected by dip-stick assay. However, other methods, wherein the tumor-specific gene product is detected by at least two different probes are also provided by the invention. For example, the invention provides a method wherein mRNA derived from a fused gene is detected by at least two nucleic acid probes, wherein at least one is directed against a mRNA fragment comprising the 5' site of the tumor-specific mRNA, and at least one other one is directed against a mRNA fragment comprising the 3' site of the tumor-specific mRNA, said fragments each corresponding to a non-tumor-specific mRNA.

Furthermore, the invention provides a method wherein protein derived from a fused gene is detected by at least two binding proteins, at least one is directed against a protein fragment comprising the amino-terminal fragment of the tumor-specific protein, and at least one other is directed against a protein fragment comprising the carboxy-terminal fragment of the tumor-specific protein, the fragments each corresponding to a non-tumor-specific protein. As an example, the invention provides a method of detecting tumor-specific gene product wherein the amino-terminal protein fragment of the gene product corresponds to the ABL or BCR protein whereas the carboxy-terminal protein fragment corresponds to the BCR or ABL protein, respectively. With this example, probes are used that have similar antigen specificities as seen for antibodies 7C6, ER-FP1, Yae, 8E9, G98-271.1.3, as shown in the experimental part herein more throughly described. Furthermore, the invention provides a method wherein protein derived from a fused gene is detected by flow cytometric detection by at least two binding proteins, wherein at least one is directed against a protein fragment comprising the amino-terminal fragment of the tumor-specific protein, and at least one other one is directed against a protein fragment comprising the carboxy-terminal fragment of the tumor-specific protein, said fragments each corresponding to a non-tumor-specific protein. As an example, the herein described bead-based sandwich antibody technique allows easy and rapid flow cytometric detection of different types of fusion proteins, preferably in a single tube assay, by using different bead-bound catching antibodies against one part of the different fusion proteins and the relevant corresponding detection antibodies against the other part of the fusion proteins.

For reasons of efficacy, it is preferred to investigate the occurrence of different fusion gene proteins simultaneously in one tube. This preference is not because a particular malignancy will have more than one fusion gene protein, but because it is convenient to have a single test tube for detection of several well-established fusion gene proteins within one disease category. Based on different flow cytometric characteristics of the beads (e.g., size, fluorochrome color, intensity of fluorochrome staining, or side scatter characteristics), multiple fusion proteins can be specifically detected in the same assay. This also includes the detection of fusion proteins from various variant translocations of the same target gene as well as fusion proteins from translocations with variant breakpoints. Of course, the herein described flow cytometric detection method can also be applied to fusion gene products of a nucleic acid nature, wherein different nucleic acid probes are labeled with different beads or fluorochromes as described herein.

The invention provides a method using probes that can be labeled or conjugated with reporter molecules, such as biotin, digyoxigenin, enzymes such as peroxidase, alkaline phosphatase, or other reporter molecules or reporter particles, such as beads, known in the art. The invention further provides a diagnostic kit comprising all the means, such as (labeled) probes or reagents or substrate or instructions, necessary to carry out the method according to the invention. Methods or diagnostic kits provided by the invention are preferably used to detect chromosomal aberrations found with certain types of cancer, for example with leukemia, be it in the detection of (residual) cancer in patients or the screening for cancer in larger populations as a whole.

DESCRIPTION OF THE FIGURES

FIG. 2. Detection of fusion proteins in malignancies. Portion A of FIG. 2 shows the detection of AML1-ETO fusion proteins derived from t(8;21) in AML. Beads labeled with different intensities of the fluorchrome phycoerythrin can be coated with different catching antibodies, e.g., directed to CBFB part of the CBFB-MYH11 fusion protein (inv(16)), the AML1 part of the AML1-ETO fusion protein (t(8;21)), or the PML part of the PML-RARA fusion protein (t(15;17)). The beads can then be incubated with a cellular lysate of a bone marrow or blood sample obtained from an AML patient, washed, and incubated with a mixture of FITC-conjugated detection antibodies directed against the other part of the indicated fusion gene proteins (see, Table 1). After washing, the beads can be analyzed by flow cytometry. As shown in portion A, one population of beads might show positivity for the relevant detection antibody, for example an FITC conjugated ETO antibody, indicating the presence of AML1-ETO fusion proteins. This would imply that the tested patient had a t(8;21) positive AML. Portion B of FIG. 2 shows the detection of the E2A-PBX1 fusion protein, derived from a precursor-B-ALL with t(1;19), using an approach comparable to that of portion A (see, Table 1 for fusion proteins).

DETAILED DESCRIPTION OF THE INVENTION

Experimental Part

The experimental part describes more in detail the invention relating to the field of leukemia, but can in no way be seen as limiting the invention.

The reciprocal translocation t(9;22)(q34;q11), observed in chronic myeloid leukemia (CML), acute lymphoblastic leukemia (ALL), and acute myeloid leukemia (AML), results from fusion between two genes: BCR and ABL. Depending on the localization of the breakpoint in the BCR gene, different tumor specific BCR-ABL genes are generated. These BCR-ABL genes are transcribed and translated in tumor-specific BCR-ABL mRNA and tumor specific BCR-ABL proteins, respectively. Hence, different diagnostic targets are available, each allowing specific diagnosis of t(9;22)(q34;q11) positive leukemia.

While conventional cytogenetics relies on detection of the characteristic chromosomal aberration (i.e., the Philadelphia chromosome: a minute chromosome 22), other techniques are used to specifically detect the BCR-ABL fusion-gene (e.g., fluorescent in situ hybridization) or the BCR-ABL fusion mRNA (e.g., reverse transcriptase polymerase chain reaction). Although all of the aforementioned techniques are well established as diagnostic techniques, none of these techniques can be easily performed on a routine and short-term basis. Yet, especially in ALL, presence of the Philadelphia (Ph) chromosome is associated with a poor prognosis. To improve the poor prognostic outcome, Ph positive ALLs require early identification to permit intensive induction regimens or alternative treatment protocols.

A new diagnostic technique is presented that is based on the exclusive detection of tumor-specific fusion-proteins. This technique is designed for identification of cancers such as Ph positive leukemias at first diagnosis in a rapid and simple fashion.

The Ph chromosome was the first karyotypic aberration found to be tumor-related. To date, the Ph chromosome is identified in various hematopoietic disorders; e.g., CML, ALL, and AML, in both adults and children.

The Ph chromosome is generated by the reciprocal translocation between the long arms of chromosome 9 and 22: t(9;22)(q34;q11) and involves the ABL gene on chromosome 9 and the BCR gene on chromosome 22. Both genes are interrupted and rearranged; resulting in a tumor-specific BCR-ABL fusion-gene on chromosome 22q- and a ABL-BCR fusion-gene on chromosome 9+.

While reports on the ABL-BCR fusion-gene are still limited, BCR-ABL fusion-genes have been extensively studied over the past two decades. Depending on the chromosomal localization of the breakpoints, different types of BCR-ABL fusion-genes have been identified. It has been demonstrated that breakpoints in the BCR gene are clustered within two regions: the major breakpoint cluster region (M-BCR), comprising five exons termed b1 to b5; and a minor breakpoint cluster region (m-BCR), located 5' of the M-BCR in the BCR-gene. In contrast, breakpoints in the ABL gene are scattered over long distances and mostly occur 5' of exon a2. In both Ph+ CML patients as well as Ph+ ALL patients breakpoints in the M-BCR are evenly distributed: either located between exon b2 and b3 or located between exon b3 and b4. Breakpoints in Ph+ ALL are, however, in majority (app. 70%) found within the m-BCR, localized in an intron between exon e1 and e2.

Because breakpoints are scattered over long distances (especially in the ABL gene), different fusion-point introns are generated within BCR-ABL genes. Although these fusion-point introns are highly variable between Ph+ patients when considering the BCR-ABL gene's fusion-point intron's length and nucleotide sequence, fusion-points of BCR-ABL transcripts are highly consistent. Thus, depending on the original BCR-ABL gene rearrangement, a single kind of BCR-ABL mRNA is usually detected: varying from a 7 kb mRNA comprising an e1a2 junction to a 8.5 BCR-ABL mRNA that either comprises a b2a2 or b3a2 junction. As the translational reading frame of BCR-ABL mRNAs is maintained, Ph+ leukemia cells express unique BCR-ABL proteins.

While Ph chromosomes are almost invariably present in CML cases, Ph chromosomes are less often detected in leukemia cells from patients suffering from AML or ALL. Still, 5% of AML cases, 25% to 30% of adults with ALL and 3% to 5% of children with ALL are diagnosed as Ph+. Reflected by a high rate of treatment failure and mortality in Ph+ leukemias, in both adults and children, Ph chromosomes are hallmarked as significant risk-factors considering treatment failure.

The importance of identifying risk-factors, such as the Ph chromosome, is beyond doubt. Current treatment protocols may be improved by identification of the t(9;22)(q11;q34) at an early time-point of the disease. At present, Ph+ leukemias are identified by a number of techniques, either detecting the aberrant chromosome, the gene, the mRNA or the aberrant protein. Yet, each of these techniques is characterized by typical specifications and limitations which should be considered before one attempts to diagnose t(9;22)(q34;q11) positive leukemias specifically.

Herein is described: an assay developed to discriminate between Ph+ leukemias and Ph— leukemias at first diagnosis in a relatively rapid and simple fashion. The underlying principle of the assay is based on detection of tumor-specific proteins by antibodies specifically reactive with fragments corresponding to the BCR-ABL fusion-proteins and to fractions of the original, non-fused BCR and ABL proteins.

Materials and methods.

Cell samples

Cell lines: Six Ph+ cell lines were used to examine the specificity of both the sepharose-Western blotting procedure as well as the BCR-ABL dipstick assay: LAMA-84 and K562, KCL-22 and BV-173, and TOM-1 and ALL/MIK. All cell lines were cultured in RPMI-1640 supplemented with 10% fetal calf serum.

Leukemic cell samples: Two leukemic cryopreserved peripheral blood samples from leukemic patients at diagnosis were used to examine the specificity of the BCR-ABL dipstick assay. Clinical and laboratory data of these patients have been described previously: one patient suffered from a Ph negative CML, with rearranged b2a2 BCR-ABL genes, the other suffered from a Ph positive precursor B-ALL, with rearranged e1a2 BCR-ABL genes.

Antibodies

All antibodies used were protein G purified and categorized as: Catching antibodies: monoclonal antibody (moAb) 7C6 (a generous gift from Dr. S. Dhut), directed towards the b2-epitope present in b2a2P210$^{BCR-ABL}$, b3a2P210$^{BCR-ABL}$, P160$^{BCR}$ and P130$^{BCR}$; moAb ER-FP1, directed towards the e1a2 fusion-point in e1a2P190$^{BCR-ABL}$ and; moAb Yae (Santa Cruz Biotechn., Santa Cruz, Calif., USA) directed towards the amino-terminus of E2A proteins. Detecting antibodies: moAb 8E9 (a generous gift from Dr. J. Wang), directed towards the SH2 domain present in e1a2P190$^{BCR-ABL}$, b2a2P190$^{BCR-ABL}$, b3a2P190$^{BCR-ABL}$ and P145$^{ABL}$ and; moAb G98-271.1.3 (a generous gift from Dr. G. Bain) directed towards the carboxyl terminus of E2A proteins. Both moAb 8E9 and moAb G98-271.1.3 were biotinylated.

Sepharose-Western blotting procedure

Cells were washed twice with ice-cold phosphate buffered saline (PBS) and lysed in ice-cold lysis buffer (1% Triton X-100, 0.05% sodium dodecyl sulphate (SDS), 150 mM NaCl, 5 mM EDTA in 10 mM sodium phosphate, pH 7.0), supplemented with 40 μl phenyl methyl sulfonyl fluoride (PMSF: 100 mM in 2-isopropanol) at a concentration of 1×10$^7$ cells/ml for 15 min. After the lysates were centrifuged in an Eppendorf centrifuge to remove insoluble material (5 min 4° C.), supernatants were split into equal volumes representing 10$^7$ cells.

Sepharose-Western blotting was performed by adding either 10 μg moAb 7C6 or 2 μg moAb ER-FP1 to the supernatant of lysed cells. Antigen-antibody reaction was allowed for two hours on a rotation device at 4° C. Next, 40 μl of an 80% (v/v) suspension of GammaBind G sepharose beads (Pharmacia Biotech AB, Uppsala, Sweden) were added. After 30 min, beads were collected and washed three times in lysis-buffer without SDS. Beads were boiled for 5 min in 60 μl sample buffer (60 mM TRIS-HCl, pH 6.8, 10% glycerol, 10 mM EDTA, 2% SDS, 2% b-mercaptoethanol and 0,03% bromophenol blue. Protein samples were subjected to 6% SDS-PAGE and transferred (Mini Protean; Bio Rad, Richmond, Calif., USA) to nitrocellulose (0.45 μm pore size; Schleicher & Schuell, Dassel, Germany). Nitrocellulose sheets were blocked in 5% non-fat dry milk powder (Protifar, Nutricia, The Netherlands) in PBS supplemented with 0.05% Tween-20 (5% MPBS).

Next, sheets were incubated for two hours at room temperature in the presence of biotinylated moAb 8E9 (2 μg/ml) in 1% MPBS. Following three washes with PBS supplemented with 0.05% Tween-20, alkaline phosphatase conjugated to streptavidin (South. Biotechn. Ass., Birmingham, Ala., USA) was added to a 1:1500 dilution and incubation was allowed to proceed for one hour. The blot was washed twice with PBS supplemented with 0.05% Tween-20 and finally with 0.15 M veronal acetate buffer, pH 9.6. For visualization of antibody-antigen complexes, we used the alkaline phosphatase substrate nitro blue tetrazolium/5-bromo-4-chloroindoxyl phosphate (NBT/BCIP; Sigma, St. Louis, Mo., USA) as previously described.

BCR-ABL dipstick method

Each catching antibody was applied as a single small spot to a (±2 cm×0.5 cm) nitrocellulose (0.45 μm pore size) strip and air dried. Each spot contained either 2 μg of moAb 7C6, 1 μg moAb ER-FP1 or 1 μg moAb Yae. Next, these nitrocellulose strips, called 'dipsticks', were rinsed in PBS supplemented with 0.05% Tween-20 and subsequently blocked in 5% MPBS (1 h, RT). At this point, dipsticks can be air dried and stored in an airtight container at 4° C. until further use.

Supernatants of cellular lysates (processed and described in the first paragraph of the above section), representing 10$^7$ cells, were added to the dipsticks. Antigen-antibody complex formation was allowed to proceed overnight at 4° C. on a rotation device. Next, dipsticks were rinsed three times in PBS supplemented with 0.05% Tween-20 and bound antigens were detected by incubating the dipstick with a mixture of biotinylated moAb 8E9 (2 μg/ml) and biotinylated moAb G98-271.1.3 (2 μg/ml), diluted in 1% MPBS. From this point on, dipsticks were further processed as described in the materials and method section of the sepharose-Western blotting procedure.

Results

To determine whether the tumor-specific BCR-ABL fusion-proteins can be exclusively recognized by immunological methods, we developed a sepharose-Western blotting procedure. A sepharose-Western blotting procedure is a combination of an immunoprecipitation reaction with a catching antibody, followed by a Western blotting procedure with a detecting antibody.

Moabs 7C6 or ER-FP1 were used as catching antibody, precipitating proteins from cellular lysates of LAMA-84 and KCL-22, or TOM-1 cells, respectively. Following immunoblotting, precipitated proteins were detected by the use of biotinylated moAb 8E9 as detecting antibodies and alkaline phosphatase conjugated to streptavidin. These sepharose-Western blotting experiments with 7C6/8E9 antibody combinations, as well as those using antibody combinations ER-FP1/8E9 enabled exclusive detection of BCR-ABL proteins. The antibody ER-FP1 combination detects e1a2P190$^{BCR-ABL}$ proteins that are not detected by the 7C6/8E9 antibody combination. Yet, the combination of 7C6/8E9 specifically detects b2a2P210$^{BCR-ABL}$ and b3a2P210$^{BCR-ABL}$ proteins, both of which are not recognized by ER-FP1 antibodies.

In conclusion, our sepharose-Western blotting data verify that tumor-specific BCR-ABL fusion-proteins are exclusively identified by the appropriate choice and mix of antibodies.

Exclusive recognition of BCR-ABL proteins in a dipstick assay

We next investigated whether the sepharose-Western blotting procedure could be simplified. By using the same sets of antibodies as were used in the sepharose-Western blotting experiments, an alternative BCR-ABL detection system, termed the BCR-ABL dipstick, was investigated for its capability identifying BCR-ABL proteins exclusively.

The BCR-ABL dipstick is made of nitrocellulose strips on which three different antibodies are immobilized: 1)

moAb7C6, 2) moAb ER-FP1 and 3) moAb Yae. To investigate whether the BCR-ABL dipstick can be used for specific identification of BCR-ABL proteins, BCR-ABL dipsticks were either incubated with cellular lysates from: 1) LAMA-84, 2) KCL-22 or 3) TOM-1 cells. Fusion-proteins that had been caught by immobilized antibodies were detected by subsequent incubation with a mixture of biotinylated moAb 8E9 (8E9-bio, recognizing the carboxyl terminus of both ABL and BCR-ABL proteins) and biotinylated moAb G98-272.1.3. (recognizing the carboxyl terminus of E2A-proteins) followed by alkaline phosphatase conjugated to streptavidin.

Incubating a BCR-ABL dipstick with either cellular lysates from LAMA-84 or cellular lysates from KCL-22, results, upon successive incubation with biotinylated antibodies (i.e. $8^E9$-bio and G98.271.1.3-bio), streptavidin-AP and its substrate, in visible dots located at the moAb 7C6 antibody spot. Incubating a BCR-ABL dipstick with cellular lysates from TOM-1, results, upon subsequent incubation with the aforementioned molecules, in a visible dot located at the ER-FP-1 antibody spot. Considering the sepharose-Western blotting data described above, these dots represent bound BCR-ABL proteins.

Together, these data demonstrate that the BCR-ABL dipstick assay can be applied for the exclusive detection of tumor-specific BCR-ABL proteins.

At this point, the BCR-ABL dipstick assay specifically detects BCR-ABL proteins in cellular lysates made from cell lines. Next, we investigated whether the BCR-ABL dipstick assay can be applied for specific diagnosis of BCR-ABL positive leukemias.

Two cryopreserved, Ficoll-enriched blood samples from patient A and patient B, respectively, with previously diagnosed BCR-ABL positive leukemias, were lysed and investigated by both the BCR-ABL dipstick assay as well as the sepharose-Western blotting procedure. The blood samples from patient A and patient B represent a Ph— CML with cryptic rearranged b3a2BCR-ABL genes and a Ph+ ALL with rearranged e1a2BCR-ABL genes, respectively. Both samples scored positive for the presence of BCR-ABL fusion-protein.

The presence of the Ph chromosome in leukemic cells is associated with poor prognosis. Especially in ALL, it is important to distinguish Ph+ leukemias from Ph— leukemias, as presence of the Ph chromosome identifies a large group of patients facing an insecure future.

Yet, this poor therapeutic outcome may be improved by an early start with more aggressive induction therapies. Therefore, sensitive and reliable diagnostic methods, identifying the Ph chromosome or its products at an early time-point of the disease, are extremely important in ALL diagnosis. At present, conventional cytogenetic analysis is the method of choice for identifying various chromosomal abnormalities in ALL. However, the results obtained by cytogenetic analysis are not always reliable since results largely depend on the number of metaphases investigated. Only institutions with special experience in ALL cytogenetics achieve successful karyotype analysis in almost every patient. Even then, some cryptic BCR-ABL rearrangements escape detection by conventional cytogenetic analysis.

Contrary to conventional cytogenetics, fluorescent in situ hybridization (FISH) techniques are not limited to the laborious analysis of metaphases. By applying probes directed against BCR and ABL genes, each labeled with a different fluorochrome, Ph+ interphase cells can be identified. Yet, depending on the co-localization of the two hybridization signals to one spot, its sensitivity is limited, because artefactual co-localization in non-malignant, normal cells may be observed.

The polymerase chain reaction (PCR) is at present the most sensitive method for detecting genetic abnormalities. In fact, molecular analysis frequently detects aberrations that are not observed karyotypically. However, as breakpoints are scattered over long distances in the tumor-specific fusion-point introns, the PCR procedure is only applicable after reverse transcription of BCR-ABL messenger RNA. Being very sensitive, strict precautions are required to prevent false positive (due to cross-contamination) and false negative (due to premature mRNA degradation) results.

Here, we describe the development of a new, simple and rapid technique based on detection of two distinct antigenic sites on the BCR-ABL fusion-protein. The combined specificity of at least two different antibodies allows for exclusive detection of BCR-ABL proteins within 24 hours.

Our assumptions concerning exclusive immunological detection of BCR-ABL proteins by the proper combination of antibodies proved correct as they were first tested in sepharose-Western blotting experiments. These experiments demonstrate that b3a2BCR-ABL and b2a2BCR-ABL proteins are specifically identified by the moAn 7C6/8E9-bio combination, while e1a2BCR-ABL proteins are specifically identified by the moAb ER-FP1/8E9-bio combination.

We next investigated whether the sepharose-Western blotting procedure could even be more simplified. The resulting BCR-ABL dipstick, a small nitrocellulose strip on which three different antibodies are immobilized, was examined for both specificity and sensitivity by using different Ph+ cell lines. The specificity was confirmed by the analysis of Ph+ cell lines: each expressing a different type of BCR-ABL protein. These results are consistent and were also observed upon testing other Ph+ cell lines such as K562, BV173 and MIK-ALL. The results show that this assay can act as an alternative screening method for detecting BCR-ABL positive leukemias at first diagnosis. Dipstick analysis of two leukemic cell samples with previously reported rearranged BCR-ABL genes, showed that initial diagnosis of BCR-ABL positive leukemias is indeed feasible. Moreover, its surplus value considering conventional cytogenetics is demonstrated by the analysis of patient A. Even though this patient suffered from Ph negative CML with cryptic rearranged BCR-ABL genes, BCR-ABL proteins were readily identified upon using the BCR-ABL dipstick assay.

Further examples

FLOW CYTOMETRIC DETECTION OF FUSION GENE PROTEINS

Background

Figure 1:
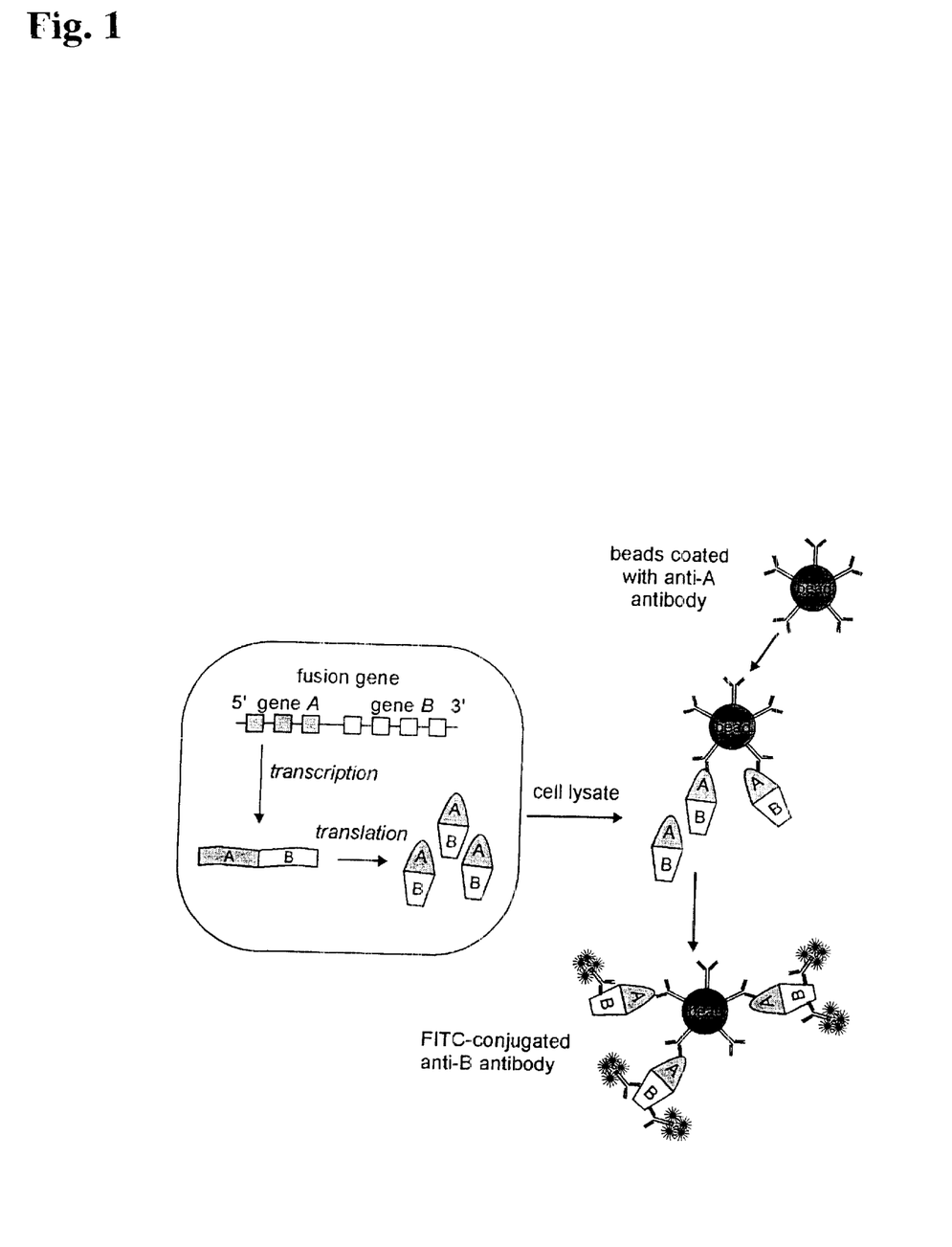
FIG. 1. Principle of the bead-based flow cytometric assay for detection of fusion proteins encoded by fusion genes of malignant cells.

Chromosomal aberrations, which are frequently present in malignant cells, can result in altered expression of genes (e.g., BCL2 protein overexpression in lymphomas with t(14;18) in which the BCL2 gene is linked to the IGH promoter) or in aberrant fusion genes (e.g., t(1;19) in which a part of the E2A gene is linked to a part of the PBX1). Fusion genes may result in the presence of fusion gene transcripts, which may subsequently be translated into fusion proteins (FIG. 1).

Chromosomal aberrations with fusion genes occur in several types of malignancies. For example, t(9;22) is found in >95% of chronic myeloid leukemias (CML) and in 25 to 40% of adult precursor-B-acute lymphoblastic leukemias (ALL), whereas t(12;21) with the TEL-AML1 fusion gene is found in approximately 25% of childhood precursor-B-

ALL. Detection of these chromosomal aberrations is of diagnostic relevance, because specific chromosomal aberrations with fusion genes can be used as PCR prognostic factors in several types of cancer, e.g., the presence of t(4;11) in infant leukemia is associated with poor outcome. In addition, chromosomal aberrations can be used as targets for monitoring the level of residual disease during and after therapy, thereby providing insight into the effectiveness of treatment. Therefore, detection of chromosomal aberrations with fusion genes is relevant for making the appropriate diagnosis, for classification, and for evaluating the effectiveness of treatment.

Chromosomal aberrations with fusion genes can be detected at several levels and by several techniques: at the DNA level (e.g., by FISH), at the mRNA level (e.g., by RT-PCR analysis), and at the protein level (e.g., by ELISA). If chromosomal aberrations with fusion genes are analyzed at the protein level, an antibody sandwich technique is used. This technique is based on a catching antibody, recognizing part of the fusion protein coded for by gene A, and a detection antibody, recognizing part of the fusion protein coded for by gene B (FIG. 1). In most cases, the catching antibody is linked to a carrier, such as a membrane (e.g., dipstick assay) or a well plate (e.g., ELISA). Although these methods in general are rapid and efficient, they are hard to incorporate into a routine hematological laboratory, because these techniques and the corresponding equipment are not readably available in such laboratories. However, flow cytometry is widely used in hematological laboratories and therefore a flow cytometric assay for detection of chromosomal aberrations would be preferred. Here we propose an assay for the analysis of chromosomal aberrations, using a detection method that is based on beads, which have the appropriate characteristics for flow cytometry.

METHOD

The principal of the proposed method is:

1. a catching antibody, recognizing part of the fusion gene protein coded for by gene A, is coupled to a particle such as a bead;
2. a cell lysate (e.g., from leukemic cells or other malignant cells) is added to the antibody-coated beads;
3. after extensive washing of the beads, the bead mixture is incubated with a detection antibody, recognizing a different part of the fusion gene protein coded for by gene B; this antibody is conjugated with a fluorochrome or any other visualization method, which is suitable for flow cytometric detection;
4. after extensive washing, the beads are analyzed by flow cytometry.

For reasons of efficacy, it will be convenient to investigate the occurrence of different fusion gene proteins simultaneously in one tube. This is not because a particular malignancy will have more than one fusion gene protein, but because it is convenient to have a single test tube for detection of several well-established fusion gene proteins within one disease category, e.g., acute myeloid leukemia (AML) or precursor-B-ALL (Table 1 and FIG. 2).

TABLE 1

Examples of combined detection of several fusion proteins in a single tube.

| Disease category | Chromosomal aberration | Fusion protein | Relative frequency children | adults |
|---|---|---|---|---|
| AML | t(8;21)(q22;q22) | AML1-ETO | 10%–14% | 6%–8% |
|  | t(15;17)(q22;q21) | PML-RARA | 8%–10% | 5%–15% |
|  | inv(16)(p13;q22) | CBFB-MYH11 | 5%–7% | 5%–6% |
| Precursor B-ALL | t(1;19)(q23;p13) | E2A-PBX1 | 5%–8% | 3%–4% |
|  | t(4;11)(q21;q23) | MLL-AF4 | 3%–5% | 3%–4% |
|  | t(9;22)(q34;q11) | BCR-ABL | 3%–6% | 25%–40% |
|  | t(12;21)(p13;q22) | TEL-AML1 | 25%–30% | 0%–2% |

Figure 2:
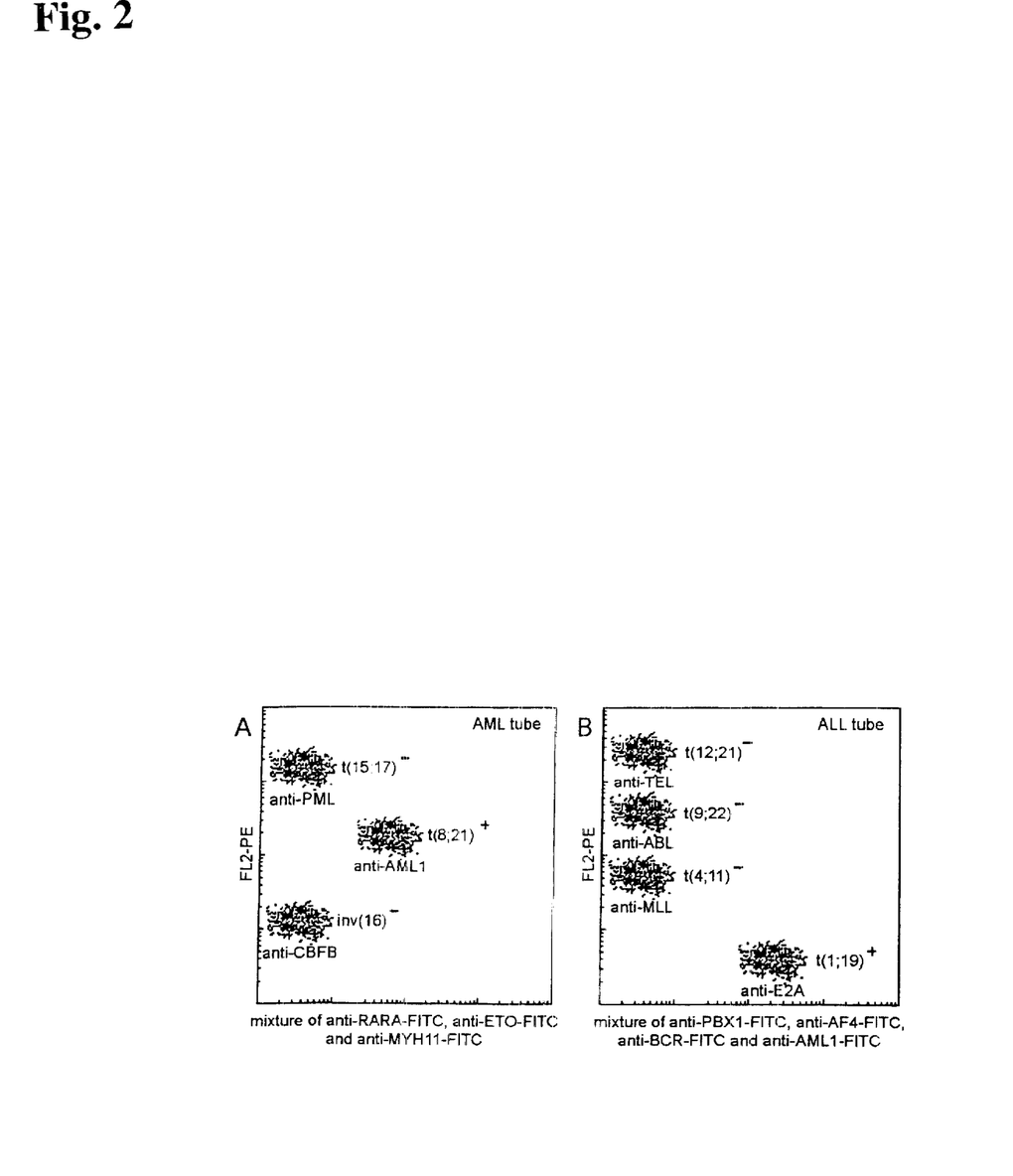

For discrimination between different types of fusion proteins, different beads are used. These beads may differ in size, conjugated fluorochrome, intensity of conjugated fluorochrome, or other bead characteristics (FIG. 2).

TABLE 2

Examples of combined detection of several different fusion proteins derived from one target gene (e.g., MLL, RARA, ALK, or EWS), which can be fused to different partner genes. The applied beads are coated with a single catching antibody and used in combination with differently conjugated detection antibodies.

| Chromosomal aberration | Fusion gene | Catching antibody on beads | Detection antibody (e.g., fluorochrome-conjugated) |
|---|---|---|---|
| MLL fusion genes in infant ALL | | | |
| t(4;11)(q21;q23) | MLL-AF4 | anti-MLL | anti-AF4 |
| t(9;11)(p21–22;q23) | MLL-AF9* | anti-MLL | anti-AF9 |
| t(11;19)(q23;19p13.3) | MLL-ENL | anti-MLL | anti-ENL |
| MLL fusion genes in AML | | | |
| t(6;11)(q27;q23) | MLL-AF6 | anti-MLL | anti-AF6 |
| t(9;11)(p21–22;q23) | MLL-AF9* | anti-MLL | anti-AF9 |
| t(10;11)(p12;q23) | MLL-AF10 | anti-MLL | anti-AF10 |
| t(11;19)(q23;19p13.1) | MLL-ELL | anti-MLL | anti-ELL |
| RARA fusion genes in AML-M3 | | | |
| t(15;17)(q22;q21) | PML-RARA | anti-RARA | anti-PML |
| t(11;17)(11q23;q21) | PLZF-RARA | anti-RARA | anti-PLZF |
| t(5;17)(q35;q21) | NPM*-RARA | anti-RARA | anti-NPM |
| t(11;17)(11q13;q21) | NUMA-RARA | anti-RARA | anti-NUMA |
| ALK fusion genes in anaplastic large cell lymphoma | | | |
| t(2;5)(p23;q35) | NPM*-ALK | anti-ALK | anti-NPM |
| t(1;2)(q25;p23) | TPM3-ALK | anti-ALK | anti-TPM3 |
| t(2;3)(p23;q21) | TFG-ALK | anti-ALK | anti-TFG |
| inv(2)(p23q35) | ATIC-ALK | anti-ALK | anti-ATIC |
| EWS fusion genes in Ewing sarcoma | | | |
| t(11;22)(q24;q12) | EWS-FLI1 | anti-EWS | anti-FLI1 |
| t(21;22)(q22;q12) | EWS-ERG | anti-EWS | anti-ERG |
| t(7;22)(p22;q12) | EWS-ETV1 | anti-EWS | anti-ETV1 |

*Some partner genes or fusion genes occur in different types of malignancies.

Figure 3:
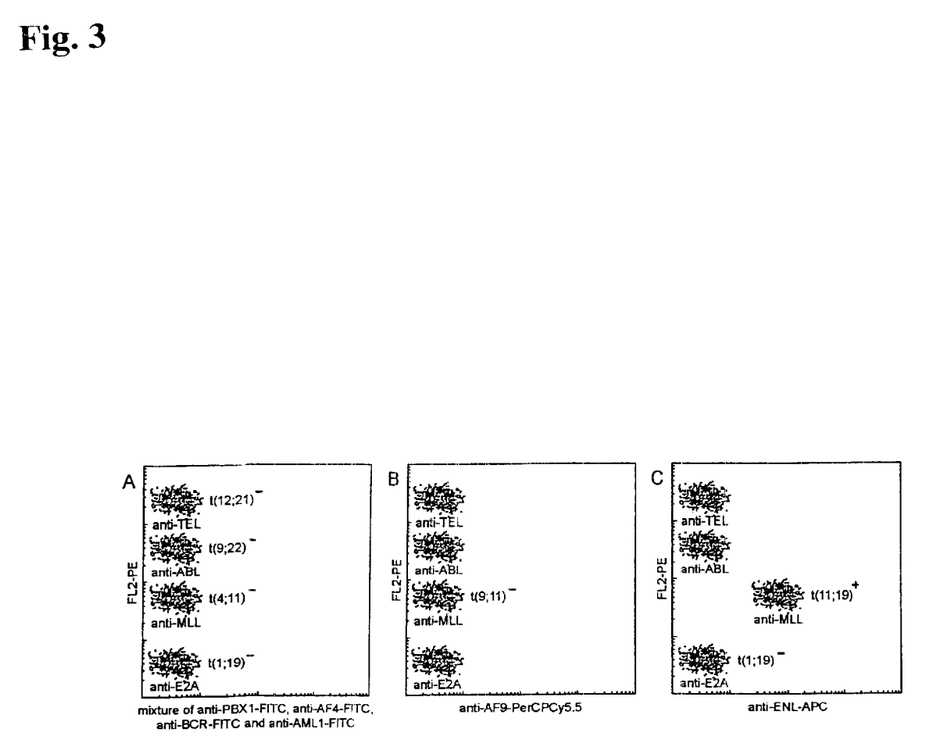
FIG. 3. Detection of an MLL gene rearrangement by the flow cytometric beads assay in an infant with precursor-B-ALL. The leukemic cells did not contain MLL-AF4 or MLL-AF9 fusion proteins (panels A and B), but panel C shows positivity for MLL-ENL fusion proteins derived from t(11;19).

In several types of malignancies, the same target gene might be involved in different variant translocations, resulting in fusion to different partner genes (Table 2). Consequently, the same target gene (e.g., MLL or EWS) produces different fusion proteins, depending on the type of variant translocation. The variant fusion proteins can be detected in a single tube assay via usage of differently labeled detection antibodies. For example the different types of fusion proteins from the variant translocations involving the MLL gene in infant precursor-B-ALL (Table 2) can be detected by use of differently conjugated AF4, AF9, and ENL antibodies (FIG. 3).

TABLE 3

Examples of combined detection of fusion protein variants, caused by different breakpoint regions, e.g., in the BCR gene of t(9;22) in CML and adult precursor-B-ALL.

| BCR breakpoint region | BCR exons expressed in fusion protein | Target regions for anti-BCR antibodies* |
|---|---|---|
| minor breakpoint region (m-bcr) | exon 1 | exon 1 |
| major breakpoint region (M-bcr) | exon 1–13 | exons 2–13 |
| micro breakpoint region (m-bcr) | exons 1–19 | exons 15–19 |

Figure 4:
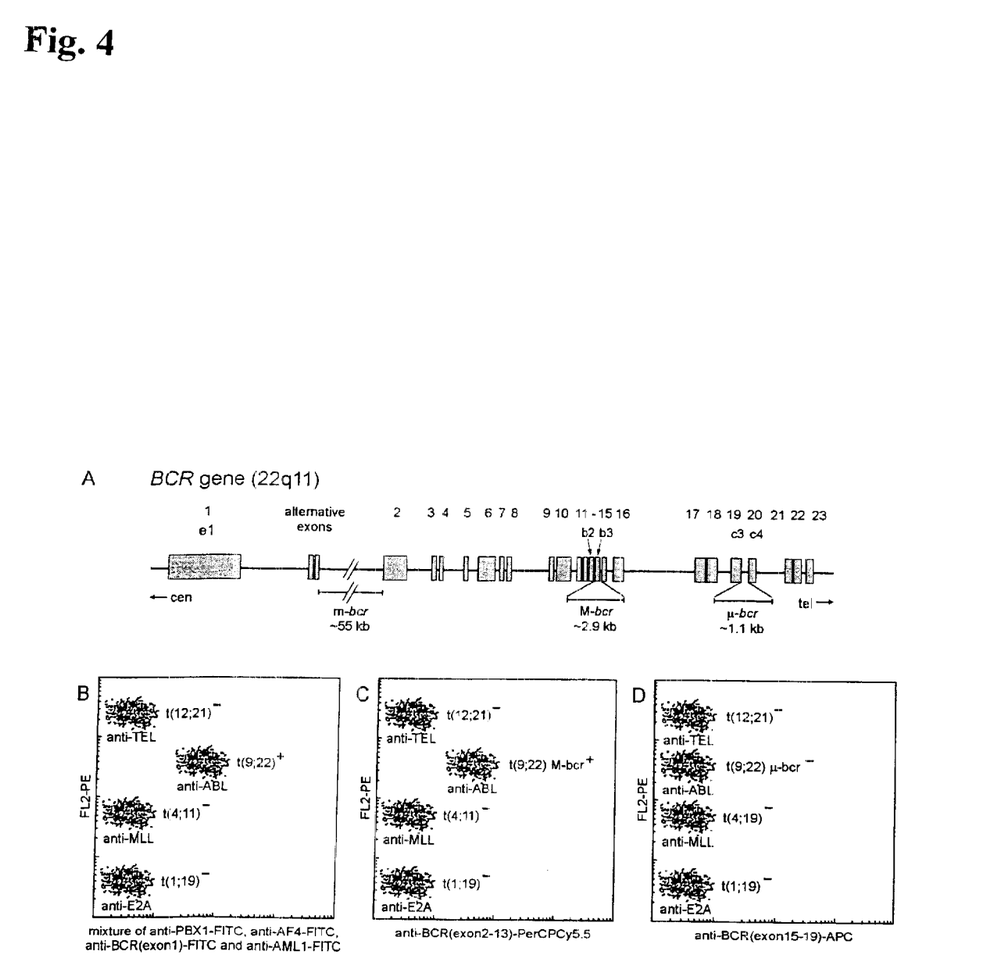
FIG. 4. The different variants of BCR-ABL fusion proteins are caused by the usage of different BCR gene breakpoints (portion A). Usage of antibodies against different BCR domains can detect three variants (panels B to D of FIG. 4). The leukemic cells of the patient in this example had t(9;22) with BCR-ABL fusion proteins (panel B). Based on the reactivity with anti-BCR (exon 1–13) but not with anti-BCR (exon 5–19) (panels C and D), it can be concluded that the BCR-ABL fusion protein is derived from t(9;22) with an M-bcr breakpoint (see Table 3).

*The anti-BCR exon 1 antibody will detect all three BCR-ABL fusion protein variants, the anti-BCR exons 2–13 antibody will detect the M-bcr and m-bcr variants, whereas the anti-BCR exon 15–19 antibody will only detect the m-bcr variant (see, FIG. 4).

Finally, some fusion proteins can occur in variant forms dependent on the breakpoint region, such as in t(9;22), t(15;17), and inv(16). For instance the BCR gene, involved in t(9;22), is known to have three breakpoint regions: major breakpoint cluster region (M-bcr), minor breakpoint cluster region (m-bcr), and micro breakpoint cluster region (m-bcr) (Table 3 and FIG. 4). Depending on the breakpoint region, several BCR exons may be present or absent in the coding regions of the different types of BCR-ABL fusion proteins. Discrimination between the three variant BCR-ABL fusion proteins is possible via antibodies, which recognize the different BCR domains, which are present in one variant form but absent in the other (see, Table 3 and FIG. 4).

The herein described bead-based sandwich antibody technique allows easy and rapid flow cytometric detection of different types of fusion proteins in a single tube assay by using different bead-bound catching antibodies against one part of the different fusion proteins and the relevant corresponding detection antibodies against the other part of the fusion proteins. Based on different flow cytometric characteristics of the beads (e.g., size, fluorochrome color, intensity of fluorochrome staining, or side scatter characteristics), multiple fusion proteins can be specifically detected in the same assay (FIGS. 2–4). This also includes the detection of fusion proteins from various variant translocations of the same target gene (Table 2 and FIG. 3) as well as fusion proteins from translocations with variant breakpoints (Table 3 and FIG. 4).

The herein presented bead-based flow cytometric technique for detection of fusion proteins is applicable on cell lysates of any malignancy with a chromosomal aberration that results in a fusion gene with the expression of the corresponding fusion protein.

REFERENCES

Carson R, Vignali D. Simultaneous quantitation of fifteen cytokines using a multiplexed flow cytometric assay. J Immunol Methods 1999; 227:41–52.

Chen R, Lowe L, Wilson J D, Crowther E, Tzeggai K, Bishop J E, Varro R. Simultaneous quantification of six human cytokines in a single sample using microparticle-based flow cytmotric technology. Clin Chem 1999; 9: 1693–1694.

Collins D P, Luebering B J, Shaut D M. T-lymphocyte functionality assessed by analysis of cytokine receptor expression, intracellular cytokine expression, and femtomolar detection of cytokine secretion by quantitative flow cytometry. Cytometry 1998; 33: 249–255.

Dimartino J F, Cleary M L. ML rearrangements in haematological malignancies: lessons from clinical and biological studies. Br J Haematol 1999;106: 614–626.

Drexler H G, Gignac S M, von Wasielewski R, Werner M, Dirks W G. Pathobiology of NPM-ALK and variant fusion genes in anaplastic large cell lymphoma and other lymphomas. Leukemia 2000;14:1533–1559.

Fulton R, McDade R, Smith P, Kienker L, Kettman J. Advanced multiplexed analysis with the FlowMetrix system. Clin Chem 1997;43: 1749–1756.

Gordon R, McFade R L. Multiplexed quantification of human IgG, IgA, and IgM with the FlowMetrix System. J Clin Invest 1997;43: 1799–1801.

McHugh T M. Flow microsphere immunoassay for the quantitative and simultaneous detection of multiple soluble analyses. Methods Cell Biol 1994; 42: 575–595.

Melnick A, Licht J D. Deconstructing a disease: RARalpha, its fusion partners, and their roles in the pathogenesis of acute promyelocytic leukemia. Blood 1999;93:3167–3215.

Naito N, Kawai A, Ouchida M, Dan'ura T, Morimoto Y, Ozaki T, Shimizu K, Inoue H. A reverse transcriptase-polymerase chain reaction assay in the diagnosis of soft tissue sarcomas. Cancer 2000; 89:1992–1998.

Oliver K G, Kettman J R, Fulton R J. Multiplexed analysis of human cytokines by use of the FlowMetrix system. Clin Chem 1998; 44: 2057–2060.

Spiro A, Lowe M, Brown D. A bead-based method for multiplexed identification and quantification of DNA sequences using flow cytometry. Appl Environ Microbiol 2000; 66:4258–4265.

van Dongen J J, Macintyre E A, Gabert J A, Delabesse E, Rossi V, Saglio G, Gottardi E, Rambaldi A, Dotti G, Griesinger F, Parreira A, Gameiro P, Diaz M G, Malec M, Langerak A W, San Miguel J F, Biondi A. Standardized RT-PCR analysis of fusion gene transcripts from chromosome aberrations in acute leukemia for detection of minimal residual disease. Report of the BIOMED-1 Concerted Action: investigation of minimal residual disease in acute leukemia. Leukemia 1999;13:1901–1928.

What is claimed is:

1. A method of detecting a chromosomal aberration in a biological sample, said method comprising:
    contacting said biological sample with at least two different probes directed against a tumor-specific protein derived from a fused gene under conditions suitable for binding of said probes to said tumor-specific protein, wherein each probe is reactive with a distinct site on said tumor-specific protein; and
    detecting by flow cytometry whether said probes bind to said tumor-specific protein, wherein if said probes bind to said tumor-specific protein, the presence of a chromosomal aberration is indicated.

2. The method according to claim 1, wherein the chromosomal aberration is associated with leukemia.

3. The method according to claim 1, wherein the chromosomal aberration is a translocation.

4. The method according to claim 3, wherein the translocation results in a Philadelphia chromosome aberration.

5. The method according to claim 1, wherein at least one of said probes is labeled with a bead.

6. The method according to claim 5, wherein at least one of said probes is labeled with a fluorochrome.

7. The method according to claim 1, wherein the tumor-specific protein comprises an amino-terminal protein fragment and a carboxy-terminal protein fragment, said amino-terminal protein fragment being derived from a first non-tumor-specific protein and said carboxy-terminal protein fragment being derived from a second non-tumor-specific protein, wherein said first and second non-tumor-specific proteins are different from one another.

8. The method according to claim 7, wherein at least one of said probes is specifically reactive with the amino-terminal protein fragment and at least one of said probes is specifically reactive with the carboxy-terminal protein fragment.

9. The method according to claim 8, wherein the amino-terminal protein fragment and the carboxy-terminal protein fragment each corresponds to a different protein selected from the group consisting of the ABL protein and the BCR protein.

10. A diagnostic kit for flow cytometric detection comprising at least a first probe and a second probe, said probes directed against a tumor-specific protein derived from a fused gene, wherein said tumor-specific protein is a gene-product of a chromosome having a chromosomal aberration thereon, and wherein each probe is reactive with a distinct site on said tumor-specific protein; and means for detecting the tumor-specific protein, wherein at least one of said probes is labeled with a bead.

11. The diagnostic kit of claim 10, wherein the chromosomal aberration is a translocation.

12. The diagnostic kit of claim 11, wherein the translocation results in a Philadelphia chromosomal aberration.

13. The diagnostic kit of claim 10, wherein at least one of said probes is labeled with a fluorochrome.

14. The diagnostic kit of claim 10, wherein the tumor-specific protein comprises an amino-terminal protein fragment derived from a first non-tumor-specific protein and a carboxy-terminal protein fragment derived from a second non-tumor-specific protein, wherein said first and second non-tumor-specific proteins are different from one another.

15. The diagnostic kit of claim 14, wherein at least one of said probes is specifically reactive with the amino-terminal protein fragment and at least one of said probes is specifically reactive with the carboxy-terminal protein fragment.

16. The diagnostic kit of claim 15, wherein the amino-terminal protein fragment and the carboxy-terminal protein fragment each is derived from a protein selected from the group consisting of the ABL protein and the BCR protein.

17. The diagnostic kit of claim 10, further comprising components for detecting the tumor-specific protein immunologically.

18. A method of detecting cancerous cells by flow cytometric detection, comprising:

providing a biological sample containing cells;

screening the biological sample for the presence of a chromosomal aberration, said screening comprising detecting a tumor-specific protein derived from a fused gene using at least two different probes directed against the tumor-specific protein, wherein said tumor-specific protein is a gene product of a chromosome having said chromosomal aberration thereon, and wherein each probe is reactive with a distinct site on said tumor-specific protein; and detecting binding of said at least two different probes to said tumor-specific protein as indicative of the presence of a chromosomal aberration, wherein at least one of said probes is labeled with a bead.

19. The method of claim 18, wherein said biological sample is selected from the group consisting of blood samples, serum samples, cells samples, tissue samples, bone marrow and biopsies.

20. The method according to claim 19, wherein the chromosomal aberration is associated with leukemia.

21. The method according to claim 18, wherein the chromosomal aberration is a translocation.

22. The method according to claim 21, wherein the translocation results in a Philadelphia chromosomal aberration.

23. The method according to claim 18, wherein at least one of said probes is labeled with a fluorochrome.

24. The method according to claim 18, wherein said tumor-specific protein derived from said fused gene is detected by at least a first and a second binding protein, said first binding protein being directed against a first protein fragment comprising the amino-terminal fragment of the tumor-specific protein, and at least a second binding protein being directed against a second protein fragment comprising the carboxy-terminal fragment of the tumor-specific protein, the first protein fragment being derived from a first non-tumor-specific protein and said second protein fragment being derived from a second non-tumor-specific protein, wherein said first and second non-tumor-specific proteins are different from one another.

25. The method according to claim 24, wherein the amino-terminal protein fragment and the carboxy-terminal protein fragment each is derived from a non-tumor-specific protein selected from the group consisting of the ABL protein and the BCR protein.

\* \* \* \* \*